United States Patent
Bezemer

(10) Patent No.: US 10,582,885 B2
(45) Date of Patent: Mar. 10, 2020

(54) DEVICE AND METHOD FOR NONINVASIVELY DETERMINING THE HEMATOCRIT VALUE OF A SUBJECT

(71) Applicant: KONINKLIJKE PHILIPS N.V., Eindhoven (NL)

(72) Inventor: Rick Bezemer, Amsterdam (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 386 days.

(21) Appl. No.: 15/312,841

(22) PCT Filed: May 6, 2015

(86) PCT No.: PCT/EP2015/059916
§ 371 (c)(1),
(2) Date: Nov. 21, 2016

(87) PCT Pub. No.: WO2015/176955
PCT Pub. Date: Nov. 26, 2015

(65) Prior Publication Data
US 2017/0202493 A1    Jul. 20, 2017

(30) Foreign Application Priority Data

May 21, 2014   (EP) .................................... 14169271

(51) Int. Cl.
*A61B 5/145*      (2006.01)
*A61B 5/0295*     (2006.01)
(Continued)

(52) U.S. Cl.
CPC ........ *A61B 5/14535* (2013.01); *A61B 5/0295* (2013.01); *A61B 5/1455* (2013.01); *A61B 5/7271* (2013.01); *A61B 2562/0233* (2013.01)

(58) Field of Classification Search
CPC .......................... A61B 5/14535; A61B 5/0295
See application file for complete search history.

(56) References Cited

U.S. PATENT DOCUMENTS

| 5,277,181 A | 1/1994 | Mendelson et al. |
| 5,553,615 A | 9/1996 | Carim et al. |

(Continued)

FOREIGN PATENT DOCUMENTS

| CN | 103610468 A | 3/2014 |
| JP | 9508291 A | 8/1997 |

(Continued)

OTHER PUBLICATIONS

Yoon, G. et al., "Development of a Compact Home Health Monitor for Telemedicine", Telemedicine and E-Health, vol. 11, No. 6, 2005, Abstract.

*Primary Examiner* — Eric F Winakur
*Assistant Examiner* — Abid A Mustansir

(57) ABSTRACT

The present invention relates to a device and method for noninvasively determining the hematocrit value of a subject. The device comprises a light source (22, 23) for emitting light onto a skin area of the subject, said light comprising first light at a first wavelength in a first wavelength range between 500 and 1000 nm and second light at a second wavelength in a second wavelength range between 1000 and 2000 nm, a reflection detector (24) for detecting light reflected from said skin area of the subject in response to light illumination by said light source, a transmission detector (25) for detecting light transmitted through said skin area of the subject in response to light illumination by said light source, a processing unit (31) for deriving plethysmography, PPG, signals for said first and second wavelengths from the light detected by said reflection detector (24) and said transmission detector (25), and an analysis unit (32) for determining the hematocrit value of the subject from said PPG signals.

11 Claims, 2 Drawing Sheets

(51) Int. Cl.
*A61B 5/1455* (2006.01)
*A61B 5/00* (2006.01)

(56) References Cited

U.S. PATENT DOCUMENTS

| | | |
|---|---|---|
| 6,006,119 A | 12/1999 | Soller et al. |
| 6,061,583 A | 5/2000 | Ishihara et al. |
| 6,266,546 B1 * | 7/2001 | Steuer ................ A61B 5/14535 600/316 |
| 6,611,320 B1 | 8/2003 | Lindberg et al. |
| 6,662,031 B1 | 12/2003 | Khalil et al. |
| 8,315,682 B2 | 11/2012 | Such et al. |
| 2002/0161287 A1 | 10/2002 | Schmitt |
| 2002/0165439 A1 | 11/2002 | Schmitt |
| 2003/0212316 A1 | 11/2003 | Leiden et al. |
| 2005/0203357 A1 | 9/2005 | Debreczeny et al. |
| 2005/0267346 A1 | 12/2005 | Faber et al. |
| 2010/0331636 A1 | 12/2010 | Huebner et al. |
| 2010/0331638 A1 * | 12/2010 | Besko ................ A61B 5/14552 600/323 |
| 2014/0058233 A1 | 2/2014 | Koyama et al. |

FOREIGN PATENT DOCUMENTS

| | | |
|---|---|---|
| JP | 2003339678 A | 12/2003 |
| WO | 9313706 A2 | 7/1993 |

* cited by examiner

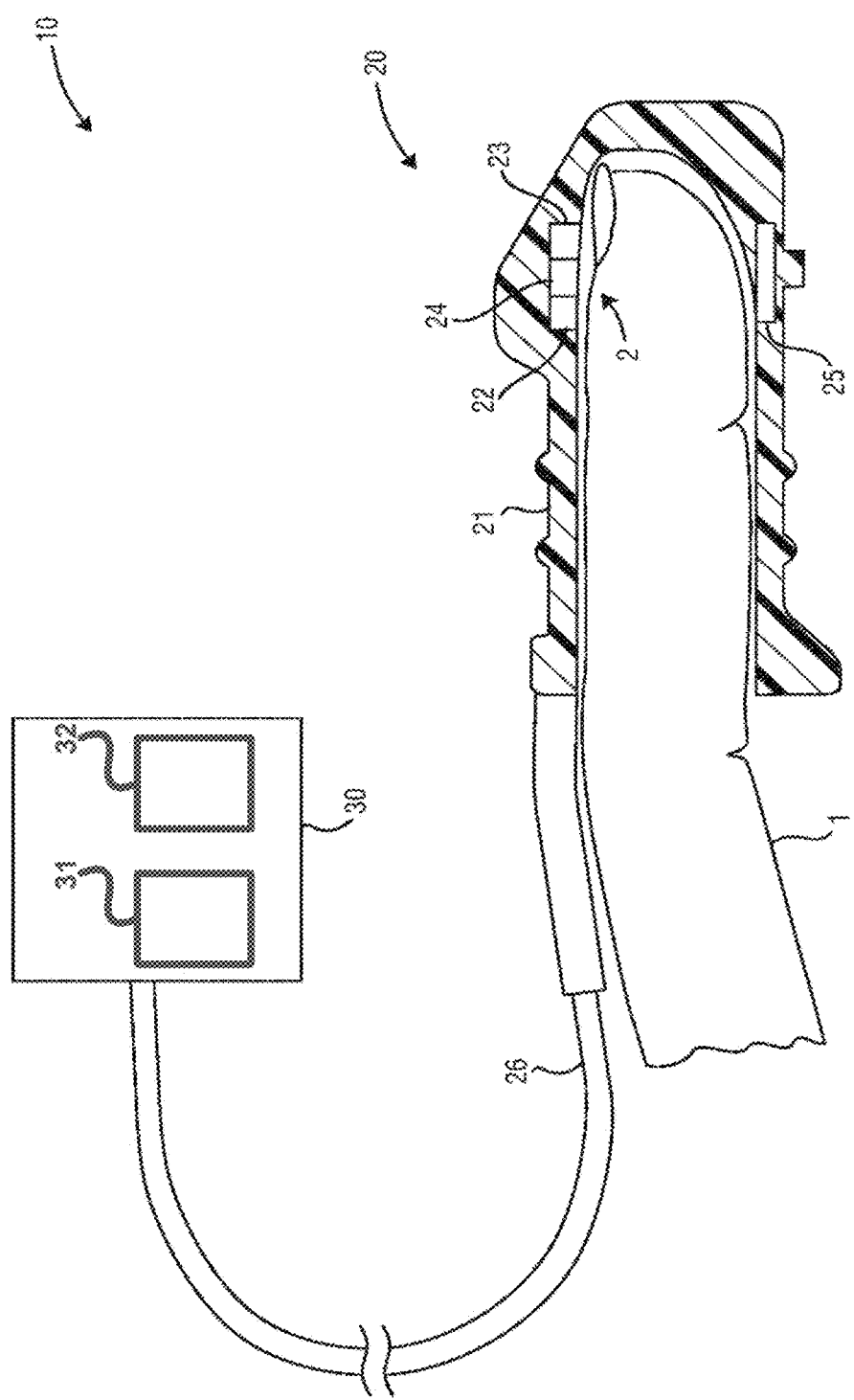

DEVICE AND METHOD FOR NONINVASIVELY DETERMINING THE HEMATOCRIT VALUE OF A SUBJECT

This application is a national stage application under 35 U.S.C. § 371 of International Application No. PCT/EP2015/059916 filed on May 6, 2015 and published in the English language on Nov. 26, 2015 as International Publication No. WO2015/176955, which claims priority to European Patent Application No. 14169271.5 filed on May 21, 2014, the entire disclosures of which are incorporated herein by reference.

FIELD OF THE INVENTION

The present invention relates to a device and method for noninvasively determining the hematocrit value of a subject, such as a person or animal. Further, the present invention relates to a processor, processing method and computer program.

BACKGROUND OF THE INVENTION

Clinicians and researchers have recognized the value of a completely noninvasive method for measurement of hematocrit or total hemoglobin concentration. U.S. Pat. No. 6,606,509 B2 discloses a device and method for measurement of hematocrit (Hct) by noninvasive means. The changes in the intensities of light of multiple wavelengths transmitted through or reflected light from the tissue location are recorded immediately before and after occluding the flow of venous blood from the tissue location with an occlusion device positioned near the tissue location. As the venous return stops and the incoming arterial blood expands the blood vessels, the light intensities measured within a particular band of near-infrared wavelengths decrease in proportion to the volume of hemoglobin in the tissue location; those intensities measured within a separate band of wavelengths in which water absorbs respond to the difference between the water fractions within the blood and the displaced tissue volume. A mathematical algorithm applied to the time-varying intensities yields a quantitative estimate of the absolute concentration of hemoglobin in the blood. To compensate for the effect of the unknown fraction of water in the extravascular tissue on the Hct measurement, the tissue water fraction is determined before the occlusion cycle begins by measuring the diffuse transmittance or reflectance spectra of the tissue at selected wavelengths.

US 2010/0331636 A1 discloses a method for the noninvasive determination of the concentration of blood constituents, in which a radiation source emits several radiation beams, each with a different wavelength. A first photo detector receives the measurement radiation of each wavelength that is reflected by a body part to be examined. A second photo detector receives the measurement radiation of each wavelength that is transmitted by the body part to be examined. The measurement radiation of each wavelength that is absorbed by the body part to be examined is then determined on the basis of the measurement of the reflected radiation by the first radiation receiver and the measurement of the transmitted radiation by the second radiation receiver. The concentration of the different constituents is calculated from the absorption of the measurement radiation that has been determined for each wavelength.

U.S. Pat. No. 6,611,320 B1 discloses a method for detecting blood characteristics including hemoglobin in a fluid medium using both transmission and reflection of a light beam which forms a quotient.

WO 93/13706 A2 discloses an apparatus and method of measuring blood hematocrit which involves directing first and second wavelengths of light through a blood sample, determining the ratio between pulsatile and non-pulsatile diffuse transmittances measured at each of the first and second wavelengths of light from the blood sample, and determining blood hematocrit of the blood sample from the ratio between pulsatile and non-pulsatile diffuse transmittances measured at each of the first and second wavelengths of light from the blood sample.

SUMMARY OF THE INVENTION

It an object of the present invention to provide an improved device and method for noninvasively determining the hematocrit value of a subject with higher accuracy and reliability. It is a further object of the present invention to provide an improved processor, processing method and computer program.

In a first aspect of the present invention a processor for noninvasively determining the hematocrit value of a subject is presented, the processor comprising:

a processing unit for deriving plethysmography, PPG, signals for a first wavelength and a second wavelength from light reflected from a skin area of the subject in response to light illumination and light transmitted through said skin area of the subject in response to said light illumination, said light illumination comprising first light at a first wavelength in a first wavelength range between 500 and 1000 nm and second light at a second wavelength in a second wavelength range between 1000 and 2000 nm, wherein said processing unit is configured to derive a first PPG signal from the reflected light at the first wavelength, a second PPG signal from the reflected light at the second wavelength, a third PPG signal from the transmitted light at the first wavelength, and a fourth PPG signal from the transmitted light at the second wavelength, and an analysis unit for determining the hematocrit value of the subject from said PPG signals, wherein said analysis unit is configured i) to determine relative pulsatile absorptions for said first to fourth PPG signals by forming a first to fourth pulsatile absorption ratio of the AC component to the DC component of the respective PPG signals, to obtain a first ratio by adding the first and third pulsatile absorption ratios obtained from the PPG signals obtained from the light at the first wavelength, to obtain a second ratio by adding the second and fourth pulsatile absorption ratios obtained from the PPG signals obtained from the light at the second wavelength, to obtain a final ratio by dividing the first ratio by the second ratio and to determine the hematocrit value of the subject from said final ratio, or ii) to determine relative pulsatile absorptions from said first to fourth PPG signals by forming a third ratio of the sum of the AC components of the first and third PPG signals and the sum of the DC components of the first and third PPG signals and by forming a fourth ratio of the sum of the AC components of the second and fourth PPG signals and the sum of the DC components of the second and fourth PPG signals, to obtain a final ratio by dividing the third ratio by the fourth ratio and to determine the hematocrit value of the subject from said final ratio.

In a further of the present invention a device is presented for noninvasively determining the hematocrit value of a subject comprising:
- a light source for emitting light onto a skin area of the subject, said light comprising first light at a first wavelength in a first wavelength range between 500 and 1000 nm and second light at a second wavelength in a second wavelength range between 1000 and 2000 nm,
- a reflection detector for detecting light reflected from said skin area of the subject in response to light illumination by said light source,
- a transmission detector for detecting light transmitted through said skin area of the subject in response to light illumination by said light source, and
- a processor as disclosed herein for processing the light detected by said reflection detector and said transmission detector for noninvasively determining the hematocrit value of the subject.

In further aspects of the present invention a corresponding method and a corresponding processing method are presented.

In yet a further aspect of the present invention a computer program is presented comprising program code means for causing a computer to carry out the steps of the processing method proposed according to the present invention when said computer program is carried out on the computer.

Preferred embodiments of the invention are defined in the dependent claims. It shall be understood that the claimed methods, device and computer program have similar and/or identical preferred embodiments as the claimed processor and as defined in the dependent claims.

The present invention is based on the following findings. Heartbeat-induced pulsatility in tissue blood volume is associated with pulsatility in the tissue's optical absorption (both red blood cells and plasma) and scattering properties (red blood cells only). More specifically, a heartbeat-induced increase in tissue blood volume leads to an increase in optical absorption and an increase in optical scattering. Light with a wavelength below 1000 nm is mainly absorbed by hemoglobin in the red blood cells and light with a wavelength above 1000 nm, in particular above 1200 nm, is mainly absorbed by the water in the plasma. Heartbeat-induced pressure waves result in a temporary increase in tissue blood volume which is associated with a temporary increase in tissue optical absorption and scattering, both in the wavelength range of hemoglobin absorption as in the wavelength range of water absorption. For hematocrit determination it is important to know how much light is absorbed by red blood cells relative to how much light is absorbed by plasma. Since light is either absorbed, forward scattered (transmitted), or backward scattered (reflected), it is insufficient to only measure one of the three (i.e. reflection or transmission) to estimate the absorption.

For pulse oximetry, a method to determine the ratio between oxyhemoglobin and deoxyhemoglobin applying one wavelength at approximately 660 nm and one wavelength at approximately 880 nm, this is not a problem because both the absorption and scattering at these wavelengths are due to the red blood cells. Hence, changes in the ratio between oxyhemoglobin and deoxyhemoglobin do not change the scattering properties at one wavelength versus the other. However, for hematocrit determination, changes in the ratio between red blood cells and plasma do change the scattering properties differently at one wavelength compared to at the other wavelength. More specifically, at wavelengths below 1000 nm, an increase in hematocrit results in an increase in absorption (decreasing the intensity of the detected light) and an increase in backscattering (also decreasing the intensity of the detected light). Both effects decrease the intensity of the detected light. At wavelengths above 1200 nm, however, the interpretation of the measured signal is less straightforward because the same increase in hematocrit results in a decrease in absorption by plasma (increasing the intensity of the detected light), but an increase in backscattering by red blood cells (decreasing the intensity of the detected light). Hence, the effects of changing hematocrit on the detected light intensity at 1450 nm are difficult to predict.

Therefore, to estimate the relative absorption by red blood cells versus that of plasma it is important to take both the forward scatter (i.e. transmission) and backward scatter (i.e. backscatter or reflection) into account as proposed according to the present invention. The transmitted light is thus not limited light that is transmitted (i.e. forward scattered) straight through the skin and tissue, but may also be scattered at a different angle, e.g. at an angle of 90° so that the transmission detector may be arranged at the side of the tissue and not, as in one embodiment, opposite to the light source.

The first wavelength lies within a first wavelength range is between 500 and 1000 nm, preferably 700 and 900 nm, and the second wavelength lies within a second wavelength range between 1000 and 2000 nm, preferably 1200 and 1500 nm. A preferred first wavelength may e.g. be 660, 800 or 880 nm, and a preferred second wavelength may e.g. be 1310 or 1450 nm. However, it shall be noted that the "first wavelength" and the "second wavelength" may not only be understood as single wavelengths, but may also be understood as small wavelength ranges covering the respective wavelengths.

In an embodiment of the device said reflection detector and said transmission detector are configured to simultaneously detect light and said processing unit is configured to derive PPG signals from simultaneously detected light.

The light source can be a single light source emitting light at different wavelengths, simultaneously or alternatingly. In an embodiment, however, said light source comprises a first light unit for emitting first light onto the skin area (i.e. a selected portion of the skin including the underlying tissue) of the subject at said first wavelength and a second light unit for emitting second light onto the skin area of the subject at said second wavelength. Said light sources, e.g. LEDs, are preferably arranged in the same housing, e.g. in a housing arranged for being mounted to a body part of the subject such as a finger clip, an ear clip or a nose clip. The two light units preferably illuminate the skin area alternatingly, e.g. at a frequency of 125 Hz. The detectors, in contrast, are preferably continuously on and detect the reflected and transmitted light simultaneously for each wavelength.

Alternating the light sources is easier to implement than making the detectors alternatingly sensitive to one wavelength or the other as required if a single light source is used that emits light at the first and second wavelength simultaneously. This can e.g. be done with a filter wheel or special crystals. A more realistic solution would be to double the amount of detectors, i.e. to use two reflection detectors and two transmission detectors, one being sensitive to the first wavelength and the other one being sensitive to the second wavelength. Sensitivity of the sensor can be determined by using optical bandpass filters.

According to one alternative of the proposed processor, said processing unit is configured to derive a first PPG signal from the reflected light at the first wavelength, a second PPG signal from the reflected light at the second wavelength, a third PPG signal from the transmitted light at the first wavelength, and a fourth PPG signal from the transmitted light at the second wavelength, and said analysis unit is configured to determine the hematocrit value of the subject from said first to fourth PPG signals.

Said analysis unit is then configured to determine relative pulsatile absorptions for said first to fourth PPG signals by forming the ratio of the AC (pulsatile) component to the DC (non-pulsatile) component of the respective PPG signals and to determine the hematocrit value of the subject from said ratios. Further, said analysis unit is configured to obtain a first ratio by adding the ratios obtained from the PPG signals obtained from the light at the first wavelength, to obtain a second ratio by adding the ratios obtained from the PPG signals obtained from the light at the second wavelength, to obtain a final ratio by dividing the first ratio by the second ratio and to determine the hematocrit value of the subject from said final ratio.

According to another alternative of the processor said analysis unit is configured to determine relative pulsatile absorptions from said first to fourth PPG signals by forming a third ratio of the sum of the AC components of the first and third PPG signals and the sum of the DC components of the first and third PPG signals and by forming a fourth ratio of the sum of the AC components of the second and fourth PPG signals and the sum of the DC components of the second and fourth PPG signals and said analysis unit is further configured to determine the hematocrit value of the subject from said third and fourth ratios. Further, said analysis unit is then configured to obtain a final ratio by dividing the third ratio by the fourth ratio and to determine the hematocrit value of the subject from said final ratio. There are, however, other ways to calculate said final ratio.

In a preferred embodiment said analysis unit is configured to use said final ratio to determine the corresponding hematocrit value from a look-up table or a calibration curve. Said look-up table or calibration curve may e.g. be acquired in advance by a calibration measurement and/or by earlier uses of the device and method.

BRIEF DESCRIPTION OF THE DRAWINGS

These and other aspects of the invention will be apparent from and elucidated with reference to the embodiments described hereinafter. In the following drawings FIG. 1 shows a schematic diagram of a device including a processor and a sensor device according to the present invention.

DETAILED DESCRIPTION OF THE INVENTION

Figure 2B:
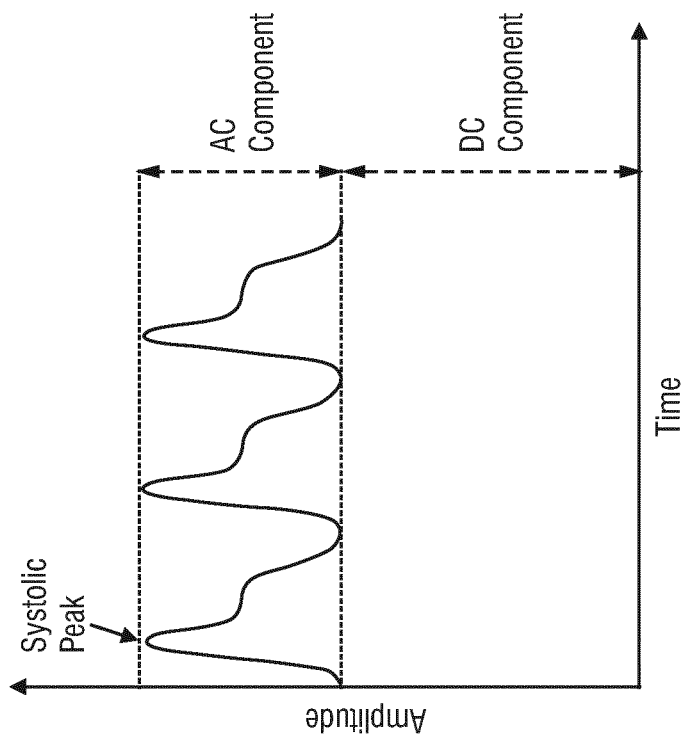
FIG. 2 shows typical PPG signals for reflection and transmission (FIG. 2B) at a wavelength below 1000 nm.

FIG. 1 shows a schematic diagram of an embodiment of a device 10 for noninvasively determining the hematocrit value of a subject, e.g. a patient, according to the present invention. The device 10 comprises a sensor device 20 (also called PPG sensor) for obtaining signals and a processor 30 for processing said signals to determine the hematocrit value of the subject. In this embodiment the sensor device 20 is configured for being mounted to the finger 1 of a person, but in other embodiments it may be configured for being mounted to a different body part such as an ala of the nose, an ear lobe or a toe. Further, in this embodiment the processor 30 is arranged separately from the sensor device 20, for instance on a separate computer, but in other embodiments the processor 30 may be configured at or within the sensor device 20, for instance as a digital signal processor.

The sensor device 20 comprises a housing 21 which fits snugly around the anatomy in question, so as to keep the sensor device 20 from falling off of the anatomy, but not so snug as to prevent circulation of blood therein.

Further, the sensor device 20 comprises a light source for emitting light onto a skin area 2 of the subject. In this embodiment the light source comprises a first light unit 22 for emitting first light onto the skin area 2 of the subject at a first wavelength and a second light unit 23 for emitting second light onto the skin area of the subject second light at a second wavelength. In other embodiment a single light source may be employed for emitting light at both wavelengths. The light source may e.g. comprise one or more LEDs. The emitted light comprises first light at said first wavelength in a first wavelength range between 500 and 1000 nm, e.g. at a first wavelength of 660, 800, or 880 nm, and second light at said second wavelength in a second wavelength range between 1000 and 2000 nm, e.g. at a second wavelength of 1310 or 1450 nm.

The first wavelength is used to take an increase in hematocrit into account that results in an increase in absorption (decreasing the intensity of the detected light) and an increase in backscattering (also decreasing the intensity of the detected light). Both effects decrease the intensity of the detected light. The second wavelength is used to take an increase in hematocrit into account that results in a decrease in absorption by plasma (increasing the intensity of the detected light) and an increase in backscattering by red blood cells (decreasing the intensity of the detected light). The same holds vice versa for a decrease in hematocrit.

The sensor device 20 further comprises a reflection detector 24 for detecting light reflected (i.e. back scattered) from said skin area 2 of the subject in response to light illumination by said light units 22, 23 and a transmission detector 25 for detecting light transmitted (i.e. forward scattered) through said skin area 2 (and underlying tissue) of the subject in response to light illumination by said light units 22, 23. The reflection detector 24 is thus arranged on the same side of the finger 1 as the light units 22, 23, while the transmission detector 25 is arranged on the opposite side. Further, the reflection detector 24 and the transmission detector 25 are configured to simultaneously detect light.

The device 10 further comprises a processor 30 for processing the signals acquired by the reflection detector 24 and the transmission detector 25. The processor 30 may be integrated within the housing of the sensor device 20 (e.g. as CMOS chip), but is preferably configured as external unit connected to the sensor device 20 by a data transmission cable 26.

The processor 30 comprises a processing unit 31 for deriving plethysmography (PPG) signals from the light detected by said reflection detector 24 and said transmission detector 25. The generation of the PPG signals is generally known in the art, e.g. from above cited document or from U.S. Pat. No. 8,315,682 B2 describing an integrated pulse oximetry sensor, and shall not be described here in more detail. Further, the processor 30 comprises an analysis unit 32 for determining the hematocrit value of the subject from said PPG signals. This can be done in various ways as will be explained below by reference to different embodiments.

To estimate the relative absorption by red blood cells versus that of plasma the device and method according to the present invention take both the forward scatter (transmission) and backward scatter (reflection) into account. In other words, both reflectance and transmittance photoplethysmography are combined into a single modality, thereby taking into account the hematocrit-dependent scattering properties of blood which differs for wavelengths below 1000 nm (absorbed by hemoglobin in red blood cells) compared to for wavelengths above 1000 nm (absorbed by water in plasma). This gives additional parameters for the hematocrit estimation, which makes it more accurate and reliable.

Figure 2A:
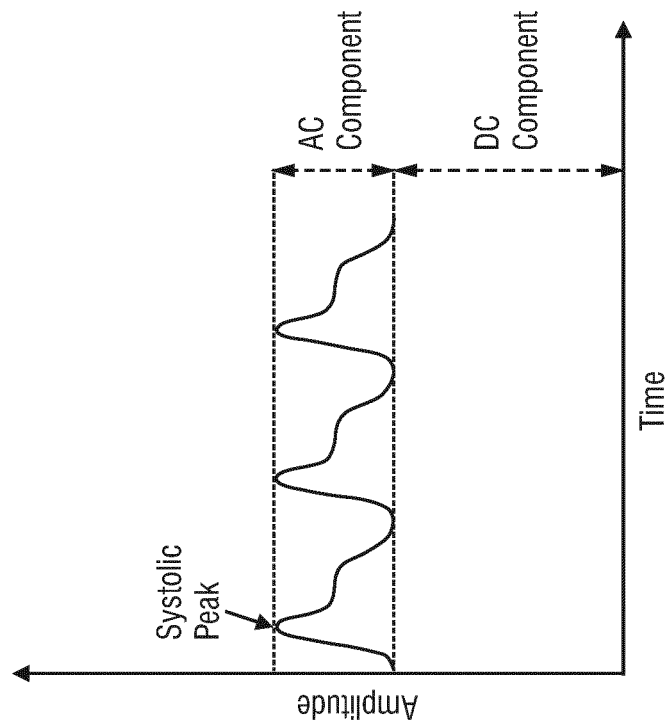

For the analysis and the determination of the hematocrit value at least two wavelengths are used to calculate the relative pulsatile absorption of hemoglobin and water. The relative pulsatile absorption Rh of hemoglobin is determined by the ratio of the AC (pulsatile) component to the DC (non-pulsatile) component of the PPG signals at a wavelength below 1000 nm, i.e. $Rh_{<1000\ nm}=(AC/DC)_{<1000\ nm}$. The relative pulsatile absorption Rw of water is determined by the ratio of the AC (pulsatile) component to the DC (non-pulsatile) component of the PPG signals at a wavelength above 1000 nm, i.e. $Rw_{>1000\ nm}=(AC/DC)_{>1000\ nm}$. FIG. 2 shows typical PPG signals for reflection (FIG. 2A) and transmission (FIG. 2B) at a wavelength below 1000 nm. In said figures the AC and DC components are indicated.

The final ratio $R=Rh_{<1000\ nm}/Rw_{>1000\ nm}$ is preferably related to the hematocrit value (Hct) by means of a lookup table or an empirically determined relation, typically in the form of Hct=a−bR. Here, a and b are constants found e.g. in calibration experiments. These constants depend on the device and system used.

In one embodiment transmission and reflection the photoplethysmography signals are combined as follows:

$$R=[(AC/DC)_{<1000\ nm,reflect}+(AC/DC)_{<1000\ nm,transmit}]/$$
$$[(AC/DC)_{>1000\ nm,reflect}+(AC/DC)_{>1000,transmit}]=$$
$$[Rh_{<1000\ nm,reflect}+Rh_{<1000\ nm,transmit}]/$$
$$[Rw_{>1000\ nm,reflect}+Rw_{>1000\ nm,transmit}]=R1/R2.$$

In other words, a first ratio R1 is obtained by adding the ratios $Rh_{<1000\ nm,reflect}$ and $Rh_{<1000\ nm,transmit}$ obtained from the PPG signals obtained from the light at the first wavelength (<1000 nm), a second ratio R2 is obtained by adding the ratios $Rw_{>1000\ nm,reflect}$ and $Rw_{>1000\ nm,transmit}$ obtained from the PPG signals obtained from the light at the second wavelength (>1000 nm), and a final ratio R is obtained by dividing the first ratio R1 by the second ratio R2. The hematocrit value of the subject is then determined from said final ratio R.

In another embodiment the transmission and reflection of photoplethysmography signals are combined as follows:

$$R=[(AC)_{<1000\ nm,reflect+transmit}/$$
$$(DC)_{<1000\ nm,reflect+transmit}]/$$
$$[(AC)_{>1000\ nm,reflect+transmit}/$$
$$(DC)_{>1000,reflect+transmit}]=R3/R4.$$

In other words, a third ratio R3 is formed of the sum of the AC components $(AC)_{<1000\ nm,reflect+transmit}$ of the first and third PPG signals and the sum of the DC components $(DC)_{<1000\ nm,reflect+transmit}$ of the first and third PPG signals, a fourth ratio R4 is formed of the sum of the AC components $(AC)_{>1000\ nm,reflect+transmit}$ of the second and fourth PPG signals and the sum of the DC components $(DC)_{>1000\ reflect+transmit}$ of the second and fourth PPG signals, and the hematocrit value of the subject is determined from said third and fourth ratios R3, R4, in particular from a final ratio R obtained by dividing the third ratio R3 by the fourth ratio R4.

There are still further embodiments to determine the final ratio.

For instance, according to another embodiment the following calculations are made:

$$DC_{<1000\ nm}=DC_{<1000\ nm,reflect}+DC_{<1000\ nm,transmit}$$

$$AC_{<1000\ nm}=AC_{<1000\ nm,reflect}+AC_{<1000\ nm,transmit}$$

$$DC_{>1000\ nm}=DC_{>1000\ nm,reflect}+DC_{>1000\ nm,transmit}$$

$$AC_{>1000\ nm}=AC_{>1000\ nm,reflect}+AC_{>1000\ nm,transmit}$$

$$R_{<1000\ nm}=AC_{<1000\ nm}/DC_{<1000\ nm}$$

$$R_{>1000\ nm}=AC_{>1000\ nm}/DC_{>1000\ nm}$$

$$R=R_{<1000\ nm}/R_{>1000\ nm}$$

$$Hct=a-b*R.$$

The present invention can be applied in different scenarios. Dehydration produces a high hematocrit that disappears when proper fluid balance is restored. Overhydration, or fluid overload, as a result of excessive fluid therapy in intensive care or surgical patients leads to hemodilution which is reflected by a low hematocrit. Hence, hematocrit is an important indicator of a patient's fluid balance.

Other groups of individuals at risk for developing anemia (i.e. low hematocrit) include infants without adequate iron intake, children going through a rapid growth spurt, during which the iron available cannot keep up with the demands for a growing red cell mass, women in childbearing years with a greater need for iron because of blood loss during menstruation, pregnant women in whom the growing fetus creates a high demand for iron, and patients with chronic kidney disease whose kidneys no longer secrete sufficient levels of the hormone erythropoietin that promotes RBC proliferation. High hematocrit can be seen in chronic smokers and in athletes that abuse the drug erythropoietin (Epogen) for blood doping purposes.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A processor for noninvasively determining the hematocrit value of a subject, the processor comprising:
   a processing unit configured to derive plethysmography, PPG, signals for a first wavelength and a second wavelength from detector signals acquired by detection of light reflected from a skin area of the subject in response to light illumination and light transmitted through said skin area of the subject in response to said light illumination,
wherein said light illumination includes a first light at a first wavelength in a first wavelength range between 500 and 1000 nm and a second light at a second wavelength in a second wavelength range between 1000 and 2000 nm, and
wherein said processing unit is further configured to derive a first PPG signal from a first detector signal acquired by detection of the reflected light at the first wavelength, a second PPG signal from a second detector signal acquired by detection of the reflected light at the second wavelength, a third PPG signal from a third detector signal acquired by detection of the transmitted light at the first wavelength, and a fourth PPG signal from a fourth detector signal acquired by detection of the transmitted light at the second wavelength; and
an analysis unit configured to determine the hematocrit value of the subject from said PPG signals, wherein said analysis unit is further configured to:
i) determine relative pulsatile absorptions for said first to fourth PPG signals by forming a first to fourth pulsatile absorption ratio of the AC component to the DC component of the respective PPG signals, to obtain a first ratio by adding the first and third pulsatile absorption ratios obtained from the PPG signals obtained from the light at the first wavelength, to obtain a second ratio by adding the second and fourth pulsatile absorption ratios obtained from the PPG signals obtained from the light at the second wavelength, and to obtain a final ratio by dividing the first ratio by the second ratio and to determine the hematocrit value of the subject from said final ratio; or
ii) determine relative pulsatile absorptions from said first to fourth PPG signals by forming a third ratio of the sum of the AC components of the first and third PPG signals and the sum of the DC components of the first and third PPG signals and by forming a fourth ratio of the sum of the AC components of the second and fourth PPG signals and the sum of the DC components of the second and fourth PPG signals, and to obtain a final ratio by dividing the third ratio by the fourth ratio and to determine the hematocrit value of the subject from said final ratio.

2. The processor of claim 1, wherein said analysis unit is configured to use said final ratio to determine the corresponding hematocrit value from at least one of a look-up table or a calibration curve.

3. A device for noninvasively determining the hematocrit value of a subject, the device comprising:
a light source for emitting light onto a skin area of the subject, said light including a first light at a first wavelength in a first wavelength range between 500 and 1000 nm and a second light at a second wavelength in a second wavelength range between 1000 and 2000 nm;
a reflection detector for acquiring detector signals by detecting light reflected from said skin area of the subject in response to light illumination by said light source;
a transmission detector for acquiring detector signals by detecting light transmitted through said skin area of the subject in response to light illumination by said light source; and
the processor of claim 1 configured for processing the detector signals acquired by said reflection detector and said transmission detector for noninvasively determining the hematocrit value of the subject.

4. The device of claim 3, wherein said reflection detector and said transmission detector are configured to simultaneously detect light and wherein said processing unit is further configured to derive PPG signals from detector signals generated from simultaneously detected light.

5. The device of claim 3, wherein said light source includes a first light unit for emitting first light onto the skin area of the subject at said first wavelength and a second light unit for emitting second light onto the skin area of the subject second light at said second wavelength.

6. The device of claim 5, wherein the two light units are configured to illuminate the skin area alternatingly.

7. A processing method for noninvasively determining the hematocrit value of a subject, the processing method comprising:
deriving plethysmography, PPG, signals for a first wavelength and a second wavelength from detector signals acquired by detection of light reflected from a skin area of the subject in response to light illumination and light transmitted through said skin area of the subject in response to said light illumination,
wherein said light illumination includes a first light at a first wavelength in a first wavelength range between 500 and 1000 nm and a second light at a second wavelength in a second wavelength range between 1000 and 2000 nm, and
wherein a first PPG signal is derived from a first detector signal acquired by detection of the reflected light at the first wavelength, a second PPG signal is derived from a first detector signal acquired by detection of the reflected light at the second wavelength, a third PPG signal is derived from a first detector signal acquired by detection of the transmitted light at the first wavelength, and a fourth PPG signal is derived from a first detector signal acquired by detection of the transmitted light at the second wavelength; and
determining the hematocrit value of the subject from said PPG signals, wherein said step of determining the hematocrit value of the subject from said PPG signals includes:
i) determining relative pulsatile absorptions for said first to fourth PPG signals by forming a first to fourth pulsatile absorption ratio of the AC component to the DC component of the respective PPG signals, obtaining a first ratio by adding the first and third pulsatile absorption ratios obtained from the PPG signals obtained from the light at the first wavelength, obtaining a second ratio by adding the second and fourth pulsatile absorption ratios obtained from the PPG signals obtained from the light at the second wavelength, and obtaining a final ratio by dividing the first ratio by the second ratio and to determine the hematocrit value of the subject from said final ratio; or
ii) determining relative pulsatile absorptions from said first to fourth PPG signals by forming a third ratio of the sum of the AC components of the first and third PPG signals and the sum of the DC components of the first and third PPG signals and by forming a fourth ratio of the sum of the AC components of the second and fourth PPG signals and the sum of the DC components of the second and fourth PPG signals, and obtaining a final ratio by dividing the third ratio by the fourth ratio and to determine the hematocrit value of the subject from said final ratio.

8. A method for noninvasively determining the hematocrit value of a subject, the method comprising:
emitting light onto a skin area of the subject, said light including a first light at a first wavelength in a first wavelength range between 500 and 1000 nm and a second light at a second wavelength in a second wavelength range between 1000 and 2000 nm;
acquiring detector signals by detecting light reflected from said skin area of the subject in response to light illumination by said light source;
acquiring detector signals by detecting light transmitted through said skin area of the subject in response to light illumination by said light source; and
in accordance with the processing method of claim 7, processing the detector signals acquired by detecting the reflected light and the transmitted light for noninvasively determining the hematocrit value of the subject.

9. A non-transitory machine-readable storage medium encoded with instructions for execution by at least one processor, the non-transitory machine-readable storage medium comprising instructions to carry out the steps of the method of claim 7.

10. A system for noninvasively determining the hematocrit value of a subject, the system comprising:
a processor configured to derive plethysmography, PPG, signals for a first wavelength and a second wavelength from detector signals acquired by detection of light reflected from a skin area of the subject in response to light illumination and light transmitted through said skin area of the subject in response to said light illumination,
wherein said light illumination includes a first light at a first wavelength in a first wavelength range between 500 and 1000 nm and a second light at a second wavelength in a second wavelength range between 1000 and 2000 nm, and
wherein said processor is further configured to derive a first PPG signal from a first detector signal acquired by detection of the reflected light at the first wavelength, a second PPG signal from a second detector signal acquired by detection of the reflected light at the second wavelength, a third PPG signal from a third detector signal acquired by detection of the transmitted light at the first wavelength, and a fourth PPG signal from a fourth detector signal acquired by detection of the transmitted light at the second wavelength; and
an analyzer configured to determine the hematocrit value of the subject from said PPG signals, wherein said analyzer is further configured to:

i) determine relative pulsatile absorptions for said first to fourth PPG signals by forming a first to fourth pulsatile absorption ratio of the AC component to the DC component of the respective PPG signals, obtain a first ratio by adding the first and third pulsatile absorption ratios obtained from the PPG signals obtained from the light at the first wavelength, obtain a second ratio by adding the second and fourth pulsatile absorption ratios obtained from the PPG signals obtained from the light at the second wavelength, and obtain a final ratio by dividing the first ratio by the second ratio and to determine the hematocrit value of the subject from said final ratio; or ii) determine relative pulsatile absorptions from said first to fourth PPG signals by forming a third ratio of the sum of the AC components of the first and third PPG signals and the sum of the DC components of the first and third PPG signals and by forming a fourth ratio of the sum of the AC components of the second and fourth PPG signals and the sum of the DC components of the second and fourth PPG signals, and obtain a final ratio by dividing the third ratio by the fourth ratio and to determine the hematocrit value of the subject from said final ratio.

11. The system of claim 10 wherein said anaylzer is further configured to use said final ratio to determine the corresponding hematocrit value from at least one of a look-up table or a calibration curve.

* * * * *